United States Patent [19]

Urbach et al.

[11] 3,969,388

[45] July 13, 1976

[54] MANUFACTURE OF ALKYLISOCYANATES

[75] Inventors: Hans Urbach, Lampertheim; Albrecht Mueller, Frankenthal, both of Germany

[73] Assignee: BASF Aktiengesellschaft, Ludwigshafen (Rhine), Germany

[22] Filed: Apr. 18, 1975

[21] Appl. No.: 569,209

[30] Foreign Application Priority Data

May 8, 1974 Germany............................ 2422211

[52] U.S. Cl............................................. 260/453 P
[51] Int. Cl.²......................................... C07C 118/00
[58] Field of Search................... 260/453 P, 453 PH

[56] References Cited
UNITED STATES PATENTS 2,480,089  8/1949  Slocombe et al................... 260/453
3,388,145  6/1968  Merz.................................... 260/453

*Primary Examiner*—Lewis Gotts
*Assistant Examiner*—Dolph H. Torrence
*Attorney, Agent, or Firm*—Johnston, Keil, Thompson & Shurtleff

[57] ABSTRACT

Alkylisocyanates are manufactured by thermal decomposition of N-alkylcarbamic acid halides in the vapor state, at not less than 20°C above their boiling points, in a plurality of reaction chambers, the bulk of the hydrogen halide formed in each reaction chamber being separated off. The products are starting materials for the manufacture of plant protection agents, pesticides, dyes, resins and plastics, textile waterproofing agents, detergents, bleaches and adhesives.

12 Claims, No Drawings

MANUFACTURE OF ALKYLISOCYANATES

The present invention relates to a process for the manufacture of alkylisocyanates by thermal decomposition of N-alkylcarbamic acid halides in the vapor state, at not less than 20°C above their boiling points, in a plurality of reaction chambers, the bulk of the hydrogen halide formed in each reaction chamber being separated off.

The manufacture of isocyanates from carbamic acid chlorides in the presence of organic bases such as tertiary amines or N,N-dialkylcarboxylic acid amides in organic solvents has been disclosed (German Published Application 1,593,554). Isocyanates can also be obtained by using aqueous solutions or suspensions of inorganic bases such as alkali metal hydroxides, alkaline earth metal hydroxides, alkali metal carbonates, alkaline earth metal carbonates or alkali metal bicarbonates (British Pat. No. 1,208,862). U.S. Pat. No. 3,465,023 expressly points out that the formation of hydrogen chloride during the manufacture of the isocyanate lowers the reactivity of the end products and therefore it is important to neutralize the acid during the process. The distillation of the isocyanate, and corrosion of the equipment, also present difficulties. The above processes have the disadvantage that the isocyanates are formed in a medium where they decompose easily. Thus Houben-Weyl, Methoden der Organischen Chemie, Volume 8, page 136 (1952) records that isocyanates dimerize in the presence of tertiary amines. They are extremely unstable toward aqueous alkali and even if stoichiometric amounts of aqueous alkali are used the isocyanates are to a large extent converted to carbamates or carbamic acids.

German Pat. No. 1,193,034 discloses the decomposition of N-alkylcarbamic acid chlorides, with alkyl of 1 to 3 carbon atoms, in an organic solvent, the hydrogen chloride formed being removed from the reaction chamber through a reflux condenser and the alkylisocyanate formed being removed from the reaction chamber at the same time via a distillation column. The solvent must boil at least 10°C above the alkylisocyanate formed. It is to be noted that isocyanates of which the boiling points are below the decomposition point of the corresponding carbamic acid chlorides cannot be manufactured by boiling the carbamic acid chlorides under reflux. Examples of such isocyanates are alkylisocyanates. The above patent teaches that whilst in such cases the carbamic acid chlorides are decomposed thermally, an equilibrium is set up and a large proportion of the hydrogen chloride recombines with the isocyanate formed, and thereby again gives the starting material. To avoid this back-reaction, alkaline compounds have hitherto been used to neutralize the hydrogen chloride. In the case of carbamic acid chlorides with alkyl of 1 to 3 carbon atoms, the above patent proposes, as a solution, that the isocyanate and hydrogen chloride be removed simultaneously from the decomposition chamber.

As is shown by the claims and the description, it is not the decomposition temperature of the alkyl compounds but the fact that the boiling point of the solvent is higher than that of the isocyanate which is essential to the invention. Example 1 shows that the simultaneous removal of hydrogen chloride and isocyanate is a decisive factor in achieving satisfactory thermal decomposition of the chloride starting material. If an alkylcarbamic acid chloride solution is merely boiled under reflux, only 43% of the expected amount of hydrogen chloride are split off, if the solution is boiled using a column without at the same time using a reflux condenser only 20% of the expected amount of hydrogen chloride are split off, whilst by the process described in German Pat. No. 1,193,034 97% are split off. The other examples, and the drawing, also place emphasis on the fact that the hydrogen chloride and isocyanate are removed simultaneously.

The object of the present invention is to provide a simpler and more economical process for making isocyanates in better yield and higher purity.

We have found that alkylisocyanates are advantageously obtained by thermal decomposition of N-alkylcarbamic acid halides by a method wherein the N-alkylcarbamic acid halide is decomposed in the vapor state in from 2 to 6 successive reaction chambers at not less than 20°C above its boiling point, and the bulk of the hydrogen halide issuing from each reaction chamber is removed before the reaction mixture, in the vapor state, enters the next reaction chamber.

Where isopropylcarbamic acid chloride is used, the reaction can be represented by the following equation:

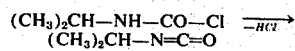
$$(CH_3)_2CH-NH-CO-Cl \xrightarrow{-HCl} (CH_3)_2CH-N=C=O$$

Compared to conventional processes, the process of the invention gives isocyanates more simply and more economically, and in better yield and higher purity. Compared to the process described in German Pat. No. 1,193,034, the process of the invention is safer in operation and easier to control. In particular, the setting, control and monitoring of the reaction pressure are substantially facilitated, especially in industrial operation and especially during decomposition of the starting material, and as a result it is possible to manage with fewer operatives, less monitoring personnel and less of the appropriate monitoring instruments Since the process according to the invention is carried out in the vapor state and in several stages, the reaction steps are more easily monitored and only one operation has to be controlled and monitored in each section of the equipment. As a result, the elimination and removal of toxic hydrogen halide becomes simple to control and this substantially assists the safety of the operation and protection of the operatives. The difficulties in respect of distillation, corrosion and reduction of the reactivity of the end products, mentioned in the above U.S. patent, play no significant role. Expensive solvents and additional bases are no longer required. These advantages are surprising since considerable reformation of the starting materials from the isocyanate and hydrogen halide and, in particular, formation of polymers or decomposition products of the heat-sensitive end products, and reactions of the end products with decomposition products during the stepwise decompositions would have been expected, from the state of the art, at the high temperatures used according to the invention. In contrast to the teaching of German Patent 1,193,034, these results are achieved in a multi-stage process wherein the hydrogen halide must in each stage be removed before isolating the end product, and at higher decomposition temperatures, the temperature being set, from the beginning of the reaction, to the decomposition temperature to be used according to the invention.

Preferred starting materials have the formula

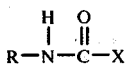

and correspondingly preferred end products have the formula

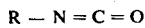

wherein R is alkyl of 1 to 10, especially of 1 to 4, carbon atoms, or alkenyl or alkynyl of 2 to 10, especially of 2 to 4, carbon atoms, and X is bromine or especially chlorine. The above radicals may in addition be substituted by groups and/or atoms which are inert under the reaction conditions, eg. alkyl of 1 to 5 carbon atoms, alkoxy of 1 to 5 carbon atoms, carbalkoxy of 2 to 5 carbon atoms, alkenyl of 2 to 5 carbon atoms or chlorine.

Examples of possible starting materials I are: methyl-, ethyl-, n-propyl-, i-propyl-, n-butyl-, i-butyl-, sec.-butyl-, t-butyl-, 2-methylbutyl-(1)-, 3-methylbutyl-(1)-, 2-methylbutyl-(2)-, 3-methylbutyl-(2)-, pentyl-(1)-, pentyl-(2)-, pentyl-(3)-, neo-pentyl-, n-hexyl-, n-octyl-, chloromethyl-, 2-chloroethyl-, 3-chloropropyl-, 4-chlorobutyl-, 6-chlorohexyl-, 1-chloropropyl-(2)-, 1-chlorobutyl-(2)-, chloro-t-butyl-, bromo-t-butyl-, 1,1-bis-chloromethyl-ethyl-(1)-, tris-chloromethyl-methyl-, allyl-, 3,3-dimethyl-allyl-(3)-, 3-methyl-3-ethyl-allyl-(3)-, butyn-(1)-yl-(3)-, 3-methyl-butyn-(1)-yl-(3)-, 3-methyl-pentyn-(1)-yl-(3)-, 2-methoxyethyl-, 2-ethoxyethyl-, 3-methoxypropyl-, 3-ethoxypropyl-, 1-methoxy-butyl-(2)-, 1-n-propoxy-propyl-(2)-, methoxy-t-butyl- and ethoxy-t-butyl-carbamic acid chloride and corresponding carbamic acid bromides.

The carbamic acid halide starting materials are passed as a stream of vapour through the reaction chambers, the residences time being advantageously from 0.01 to 15 minutes and preferably from 0.1 to 5 minutes per reaction chamber. Since a high proportion of the starting material is decomposed to alkylisocyanate even in the first reaction chamber, the above residence time relates in each case to the total amount of starting material and end product formed from it in the reaction chamber. The starting material may be introduced into the reaction by, eg., evaporating a solution of the material in a solvent and passing the vapor into the first reaction chamber of the invention. It is expedient to use the mixture of solvent and carbamic acid halide obtained from the manufacture of the starting material by reaction of aliphatic amine with phosgene. Mixtures of different starting materials and mixtures of the starting materials with the corresponding isocyanates may also be used. Examples of solvents which may be used are aromatic hydrocarbons such as toluene, xylene or chlorohydrocarbons such as chlorobenzene. By appropriate choice of the solvent, it is possible to control the vaporization so that only the starting material, without significant amounts of solvent, enters the first reaction chamber. In such cases it is advantageous if, before the vapor enters the first reaction chamber, any hydrogen halide which it may contain as a result of decomposition is removed entirely or partially, eg. through a reflux condenser which is suitably at from −10°C to 20°C.

In some cases, eg. when manufacturing methylisocyanate or isopropylisocyanate, it is expedient to mix the vapor of the starting materials with gases which are inert under the reaction conditions. Suitable inert gases to use are xenon, argon, neon and helium, alkanes such as methane, ethane, propane, 2,2-dimethylpropane, butane, pentane and isobutane, gaseous halogenohydrocarbons such as tetrafluoromethane, dichloromethane, chloromethane, bromomethane, hexafluoroethane, chloroethane and fluoroethane, gaseous organic compounds of inorganic elements, such as tetramethylsilane, ethers such as dimethyl ether and methyl ethyl ether and, preferably, nitrogen, oxygen, air and/or carbon dioxide, as well as mixtures thereof. In a suitable embodiment of the process, at least 80, preferably from 150 to 10,000, and especially from 200 to 8,000, parts by volume of inert gas may be used per part of starting material II. It is possible to decompose the starting material and only mix the inert gas with the vapor of starting material during the decomposition, eg. from 0.5 to 2 hours after commencement of the decomposition of the starting material; however, it is more advantageous to introduce the inert gas ab initio, ie. from the start of the decomposition. If the inert gas is recycled it is expedient to free it from hydrogen halide, for example by absorbing the latter in water to form hydrochloric acid, before the gas re-enters the decomposition mixture.

The decomposition is carried out in 2 to 6, preferably 2, 3 or 4, successive reaction chambers. Between any 2 reaction chambers, the bulk of the hydrogen halide issuing from one chamber is removed, expediently through a branch line, eg. a laterally attached pipe fitted with a reflux condenser, before entering the next chamber. All the reflux condensers are preferably cooled to from 100° to 150°C. In the case of the 2nd and subsequent reaction chambers, the hydrogen halide which issues from the chamber may have been freshly formed by decomposition or may originate from the decomposition in one of the preceding reaction chambers. By packing the reaction chambers, it is possible to reduce the proportion of hydrogen halide passing through them and correspondingly to increase the main portion which is removed through the branch line fitted with a reflux condenser. The percentages by weight of the hydrogen halide, issuing from any particular reaction chamber, which are removed through the branch line are more than 50, advantageously from 60 to 95, for each chamber, and specifically from 60 to 85 after the first reaction chamber, from 60 to 85 after the 2nd reaction chamber, from 60 to 95 after the 3rd reaction chamber and from 60 to 95 after the 4th, 5th and 6th reaction chambers.

The decomposition is advantageously carried out at from 20° to 80°C, preferably from 20° to 60°C, and suitably from 20° to 40°C, above the boiling point of the N-alkylcarbamic acid halide, in numerous cases, in particular at from 95° to 160°C and advantageously at from 95° to 140°C, under atmospheric or superatmospheric pressure, batchwise or, preferably, continuously; eg. in the case of the manufacture of ethylisocyanate the temperature exceeds the boiling point of the N-alkylcarbamic acid halide by from 25° to 30°C in the first reaction chamber, from 30° to 40°C in the 2nd reaction chamber, from 20° to 30°C in the 3rd reaction chamber and from 20° to 30°C in the 4th to 6th reaction chamber. Preferably, the reaction chambers used are reacted tubes of from 20 to 1,000 millimeters diameter and from 100 to 2,000 millimeters length, containing packings of from 10 to 50 millimeters diameter, or reaction tubes with diameters of from 2 to 100 millimeters and lengths of from 100 to 2,000 millimeters which are subdivided into from 2 to 6 chambers through which the mixture flows continuously and successively. As packings it is possible to use, eg., Raschig rings, Intos rings, Prym rings, Pall rings, Berl saddles, Intalox saddles, Torus saddles, Interpack elements, Stedman packings, oblique-film elements, Haltmeier rolls, twin packings, Wilson spirals or Branunschweig helices.

The reaction may be carried out as follows: the starting material, as a vapor optionally mixed with an inert gas, is passed through the reaction chambers at the decomposition temperature and before entering any one reaction chamber the bulk of the hydrogen halide contained in the mixture is removed via a branch line fitted with a reflux condenser. The temperature of the condenser is as a rule below the boiling point of the end product formed. Before entering the first reaction chamber, a branch line fitted with a reflux condenser may also be used to remove phosgene, or hydrogen chloride, entrained from the process of manufacture of the carbamic acid chloride. Preferably, a fractionating device is provided after the last reaction chamber; this retains residual carbamic acid chloride which runs back into the last reaction chamber where it is again vaporized and decomposed. At the top of the fractionating device, the pure end product issues, at times together with minor amounts of hydrogen halide. It is desirable to provide a further branch line with reflux condenser between the last reaction chamber and the fractionating device in order to remove the last amounts of hydrogen halide. Any desired distillation apparatuses may be used as the fractionating devices, eg. perforated tray columns, Oldershaw columns, glass tray columns, bubble tray columns, valve tray columns, thin-film evaporators and falling-flow distillation apparatuses.

The isocyanates which may be manufactured by the process of the invention are valuable starting materials for the manufacture of plant protection agents, pesticides, dyes, resins and plastics, textile waterproofing agents, detergents, bleaches and adhesives. Their conversion to urethanes, eg. for use as foams or very flexible high molecular weight coatings, or to ureas, is of particular importance. For details of their uses, reference may be made to the publications cited earlier and to Ullmanns Encyklopädie der techischen Chemie, Volume 9, pages 11, 12 and 404, and Volume 17, page 204.

The parts mentioned in the Exampes are by weight and bear the same reflection to parts by volume as the kilogram to the liter.

EXAMPLE 1

1,000 parts of isopropylcarbamic acid chloride are vaporized in a still and passed in the course of 5 hours through 3 reaction chambers of equal length, in the shape of reaction tubes. The decomposition temperature is 120°C in chamber 1, 120°C in chamber 2 and 120°C in chamber 3. Each reaction chamber is preceded by a branch line fitted with a reflux condenser, through which hydrogen chloride is removed in the course of 5 hours. Behind the 3rd reaction chamber there is a further branch line through which the last remnants of hydrogen chloride are removed in the same period of time, and a fractionating column kept at 74°C. 668 parts (95.8% of theory) of isopropyl isocyanate boiling at 74°C are obtained, in a purity of 99% by weight, as the end product at the top of the column.

EXAMPLE 2

1,000 parts of methylcarbamic acid chloride are vaporized in a still and passed in the course of 5 hours through 3 reaction chambers of equal length, in the shape of reaction tubes. The decomposition temperature is 105°C in chamber 1, 105°C in chamber 2 and 105°C in chamber 3. Each reaction chamber is preceded by a branch line fitted with a reflux condenser, through which hydrogen chloride is removed in the course of 5 hours. Behind the 3rd reaction chamber there is a further branch line through which the last remnants of hydrogen chloride are removed in the same period of time, and a fractionating column kept at about 40°C. 654 parts (91.8%) of theory) of methyl isocyanate boiling at 38 to 40°C are obtained, in a purity of 95% by weight, as the end product at the top of the column.

We claim:

1. A process for the manufacture of alkylisocyanates by thermal decomposition of N-alkylcarbamic acid halides, wherein the N-alkylcarbamic acid halide is decomposed in the vapor state in from 2 to 6 successive reaction chambers at not less than 20°C above its boiling point, and the bulk of the hydrogen halide issuing from each reaction chamber is removed before the reaction mixture, in the vapor state, enters the next reaction chamber.

2. A process as claimed in claim 1, wherein the decomposition is carried out using a residence time of from 0.01 to 15 minutes per reaction chamber.

3. A process as claimed in claim 1, wherein the decomposition is carried out with a mixture of solvent and carbamic acid halide.

4. A process as claimed in claim 1, wherein the decomposition is carried out with from 150 to 10,000 parts by volume of inert gas per part of starting material I.

5. A process as claimed in claim 1, wherein the decomposition is carried out in 2, 3 or 4 successive reaction chambers.

6. A process as claimed in claim 1, wherein from 60 to 95% by weight of the hydrogen halide issuing from the particular reaction chamber is removed through a branch line.

7. A process as claimed in claim 1, wherein the percentages by weight of the hydrogen halide issuing from any particular reaction chamber which are removed through the branch line are from 60 to 85 after the first reaction chamber, from 60 to 85 after the 2nd reaction chamber, from 60 to 95 after the 3 rd reaction chamber and from 60 to 95 after the 4th, 5th and 6th reaction chambers.

8. A process as claimed in claim 1, wherein the decomposition is carried out at a temperature of from 20° to 80°C above the boiling point of the N-alkylcarbamic acid halide.

9. A process as claimed in claim 1, wherein the decomposition is carried out at a temperature of from 20° to 60°C above the boiling point of the N-alkylcarbamic acid halide.

10. A process as claimed in claim 1, wherein the decomposition is carried out at a temperature of from 20° to 40°C above the boiling point of the N-alkylcarbamic acid halide.

11. A process as claimed in claim 1, wherein the decomposition is carried out at from 95° to 160°C.

12. A process as claimed in claim 1, wherein the decomposition is carried out at from 95° to 140°C.

* * * * *